United States Patent [19]

Billmers

[11] Patent Number: 5,004,791
[45] Date of Patent: Apr. 2, 1991

[54] ORGANOSILOXANE-CONTAINING POLYSACCHARIDES

[75] Inventor: Robert L. Billmers, Stockton, N.J.

[73] Assignee: National Starch and Chemical Investment Holding Corporation, Wilmington, Del.

[21] Appl. No.: 580,438

[22] Filed: Sep. 10, 1990

Related U.S. Application Data

[62] Division of Ser. No. 318,579, Mar. 3, 1989, Pat. No. 4,973,680.

[51] Int. Cl.$^5$ .................. C08B 11/00; C08B 37/16; C08B 31/02; C08B 33/02
[52] U.S. Cl. ................... 527/300; 527/313; 527/314; 428/364; 428/391; 428/393; 428/394; 162/164.1; 162/175; 162/177; 162/178
[58] Field of Search .............. 527/300, 313, 314; 428/364, 391, 393, 394; 162/164.1, 175, 177, 178

[56] References Cited

U.S. PATENT DOCUMENTS

| | | |
|---|---|---|
| 3,071,492 | 1/1963 | Satterly .................. 117/100 |
| 3,167,468 | 1/1965 | Lovelace et al. .......... 161/175 |
| 3,227,192 | 1/1966 | Griffiths ................. 139/420 |
| 3,398,015 | 8/1968 | Buckler et al. ........... 117/126 |
| 3,481,771 | 12/1969 | Doering ................. 117/126 |
| 3,615,311 | 10/1971 | Ignatius ................. 117/126 |
| 3,664,855 | 5/1972 | Morrison et al. .......... 106/212 |
| 3,793,065 | 2/1974 | Morrison et al. .......... 117/126 |
| 3,928,666 | 12/1975 | Morrison et al. .......... 428/378 |
| 4,166,872 | 9/1979 | Karpik et al. ............ 428/35 |
| 4,168,345 | 9/1979 | de Massey et al. ......... 428/441 |
| 4,259,190 | 3/1981 | Fahey .................... 252/8.6 |
| 4,490,526 | 12/1984 | Amort et al. ............. 536/102 |
| 4,500,600 | 2/1985 | Wong et al. .............. 428/391 |
| 4,775,725 | 10/1988 | DePasquale et al. ........ 525/403 |
| 4,780,339 | 10/1988 | Lacourse et al. .......... 427/389.7 |
| 4,839,449 | 6/1989 | Billmers et al. .......... 526/238.2 |
| 4,973,680 | 11/1990 | Billmers ................. 536/58 |

FOREIGN PATENT DOCUMENTS 0305833 3/1989 European Pat. Off. .
932685 7/1963 United Kingdom .

Primary Examiner—Nathan M. Nutter
Attorney, Agent, or Firm—Mary E. Porter; Edwin M. Szala

[57] ABSTRACT

Disclosed are a polysaccharide derivative having the structure:

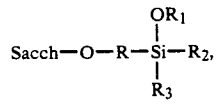

and a polysaccharide graft polymer having the structure: Sacch—O—(G)$_m$—(M)—$_n$, wherein Sacch- is a polysaccharide; m is zero or one; G is the residue of a polymerizable, unsaturated monomer which is bonded to the polysaccharide in an ether or ester linkage; n is greater than one; M is the residue of one or more polymerizable, unsaturated, monomer(s), at least one of which is a siloxane-containing monomer, which have been grafted to the polysaccharide by free radical polymerization; R is an organic group which is bonded to the polysaccharide by an ether or ester linkage and to the silicon by a carbon-silicon linkage; R$_1$ is a straight or branched C$_1$-C$_6$ alkyl or alkenyl group, or an aryl, aralkyl or alkaryl group; and R$_2$ and R$_3$ are, independently, straight or branched C$_1$-C$_6$ alkyl or alkenyl groups, or aryl, aralkyl or alkaryl groups, or alkoxides of straight or branched C$_1$-C$_6$ alkyl or alkenyl groups, or aryl, aralkyl or alkaryl groups, or alkoxides wherein R$_2$ and R$_3$ together form a cyclic structure of at least five members. The siloxane-containing polysaccharide derivatives and polysaccharide graft polymers are useful in glass fiber forming size compositions, in paper making and in other applications.

12 Claims, No Drawings

ORGANOSILOXANE-CONTAINING POLYSACCHARIDES

This application is a division, of application Ser. No. 07/318,579, filed Mar, 3, 1989 and now U.S. Pat. No. 4,973,680.

BACKGROUND OF THE INVENTION

This invention relates to polysaccharide derivatives and polysaccharide graft polymers which contain organosiloxane substituents. These compositions are prepared by reacting a polysaccharide with a di-functional reagent which contains a siloxane group and a group which will react with a polysaccharide. The polysaccharide-reactive group of the reagent forms an ether or ester linkage with the polysaccharide, thereby attaching a reactive siloxane group to the polysaccharide. These organosiloxane-containing polysaccharides are employed in glass fiber size composition compositions to improve size adhesion to glass fibers, in paper-making to increase dry strength in paper, and the like.

Other silicon-containing polysaccharide compositions are known. In one class of such compositions, the silane group is bonded directly to a hydroxyl group of the polysaccharide. The compositions are prepared by first hydrolyzing the siloxane functionality of the reagent to the corresponding silanol, and then reacting the silanol with starch. One member of this class of starch organosilanes forms more viscous aqueous dispersions than unmodified starches and is useful for the hydrophobation of cellulosic materials, and as binders for mineral fibers, textile additives, paper sizes and plastic fillers. See U.S. Pat. No. 4,540,777. Other starch organosilanes are hydrophobic and free-flowing. See U.S. Pat. No. 3,071,492. Such compositions are not useful in applications taught herein which require the presence on the polysaccharide of siloxane substituent(s) that are available for further reaction.

Silicone-containing amylose films have been prepared by contacting the surface of a preformed amylose film with organo-silicon halides. See U.S. Pat. No. 3,398,015. The silicon is bonded directly to the amylose, and the amylose-silicone films are reported to exhibit hydrophobic properties.

Organosiloxane-containing polysaccharide derivatives wherein the siloxane group is available as a reactive group are taught in commonly assigned, co-pending, U.S. patent application Ser. No. 112,634, to Billmars, et al., filed Oct. 26, 1987. However, unlike the compositions disclosed herein, the derivatives disclosed in that application require a two step, dual reagent process for preparation, and the products of that process are limited to divalent aromatic group containing, nitrogen-containing derivatives. Thus, the derivatives and polymers disclosed herein offer advantages of greater flexibility, process efficiency, reagent availability and reduced costs over known organosiloxane-containing polysaccharides.

The present invention also relates to a glass fiber forming size composition, comprising the organosiloxane-containing polysaccharides of this invention; and to a method for preparing glass fibers, and, in particular, to the application of the forming size to continuous filament glass fiber strands.

In glass fiber production, molten glass flows or is pulled through tiny orifices or tips in a heated platinum bushing. The individual glass filaments are passed through a sizing bath, grouped into a strand, and then wound on a rapidly rotating forming tube. The size is applied to the filaments in order to bind them together, maintain the integrity of the strand during winding and unwinding, and facilitate eventual processing. The strand on the forming tube is thereafter placed in an oven to dry or is allowed to air dry to reduce the moisture content of the strand.

Many different compositions have been used as glass forming sizes. Typically, the sizes have comprised aqueous dispersions of various modified and unmodified starches and oils. Numerous patents are directed to starch- or other polysaccharide-containing glass fiber size compositions. Illustrative patents include U.S. Pat. Nos. 3,227,192; 3,167,468; 3,481,771; 3,664,855; 3,793,065; 3,928,666; and 4,168,345. Typical polysaccharide-containing glass fiber forming size compositions which are useful herein are disclosed in U.S. Pat. Nos. 3,615,311; 4,166,872; 4,780,339; and 4,259,190, the disclosures of which are hereby incorporated by reference.

In addition, U.S. Pat. No. 4,500,600 (issued Feb. 19, 1985 to Wong et al.) discloses glass fibers coated with a size containing gamma-aminopropyltriethoxysilane and a selected alkoxysilane, and a method for making such fibers. Unlike the sizes disclosed herein, the Wong et al. sizes do not bond a polysaccharide to the glass, and the fibers made with the Wong et al. size are designed for use in reinforced plastics. They are not suited for applications requiring significant adhesion of the size to the glass fiber.

There remains a need for new polysaccharide derivatives, especially derivatives containing silane groups which are useful in glass forming sizes and which display improved adhesion to glass.

SUMMARY OF THE INVENTION

The present invention provides a polysaccharide derivative having the structure:

wherein Sacch- is a polysaccharide molecule; R is an organic group which is bonded to the polysaccharide by an ether or ester linkage and to the silicon by a carbon-silicon linkage; $R_1$ is a $C_1$-$C_6$ alkyl or alkenyl group, or an aryl, aralkyl, or alkaryl group; and $R_2$ and $R_3$ are, independently, $C_1$-$C_6$ alkyl or alkenyl groups, or aryl, aralkyl or alkaryl groups, or alkoxides of $C_1$-$C_6$ alkyl or alkenyl groups, or aryl, aralkyl or alkaryl groups, or alkoxides wherein $R_2$ and $R_3$ together form a cyclic structure of at least five members. The alkyl and alkenyl chains may be straight or Also provided is a polysaccharide graft polymer, having the structure:

wherein Sacch- is a polysaccharide; m is zero or one; G is the residue of a polymerizable, unsaturated monomer which is bonded to the polysaccharide by an ether or ester linkage; n is greater than one; and M is the residue of one or more polymerizable, unsaturated, monomer(s), at least one of which is a siloxane-containing monomer, which have been grafted to the polysaccharide by free radical polymerization. M may take the form:

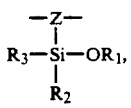

wherein Z is the residue of a polymerizable, unsaturated organic group which is bonded to the silicon by a carbon-silicon linkage; $R_1$ is a $C_{1-6}$ alkyl or alkenyl group, or an aryl, aralkyl or alkaryl group; and $R_2$ and $R_3$ are, independently, $C_{1-6}$ alkyl or alkenyl groups, or aryl, arakyl or alkaryl groups, or alkoxides of $C_{1-6}$ alkyl or alkenyl groups, or aryl, aralkyl or alkaryl groups, or alkoxides wherein $R_2$ and $R_3$ together form a cyclic structure of at least five members. The alkyl and alkenyl chains may be straight or branched.

The organosiloxane-containing starch derivatives and graft polymers of this invention are useful in glass forming size compositions. Thus, this invention provides a glass size composition, comprising 40-70% of an aqueous dispersion of the organosiloxane starch compositions, 15-40% of a nonionic oil, 2-8% of an emulsifier, and 5-15% of a cationic lubricant, together with a method for sizing glass fibers employing this size composition and glass fibers produced by this method.

The organosiloxane-containing polysaccharides of this invention are also useful in paper making and in a variety of compositions in which modified polysaccharides are employed, including, but not limited to, adhesives, thickeners, sealants, coatings, binders and films. Thus, a method of making paper employing the organosiloxane-containing polysaccharides of this invention, and paper made thereby, are provided herein.

DESCRIPTION OF THE PREFERRED EMBODIMENTS

Starches which may be used herein may be derived from any source, including corn, potato, sweet potato, wheat, rice, sago, tapioca, waxy maize, sorghum, high amylose corn, or the like. Starch flours also may be used. Also useful herein are the conversion products derived from any of these starches including, for example, dextrins prepared by the hydrolytic action of acid and/or heat; oxidized starches prepared by treatment with oxidants such as sodium hypoohlorite; fluidity or thin-boiling starches prepared by enzyme conversion or mild acid hydrolysis; and derivatized (e.g., cationic, anionic, amphoteric, and non-ionic) starches and cross-linked starches. The starch may range from a granular form to a fully gelatinized form (i.e., cooked, non-granular starch).

Gums which may be used herein include polygalactomannans, which are heteropolysaccharides composed principally of long chains of 1,4-beta-D-mannopyranosyl units to which single unit side chains of alpha-D-galactopyranosyl units are joined by 1,6-linkages. Also useful herein are degraded gum producers resulting from the hydrolytic action of acid, heat, shear, and/or enzyme; oxidized gums; and derivatized gums. The preferred gums include guar gum and locust bean gum because of their commercial availability.

Other polysaccharides useful herein include cellulose and cellulose derivatives, especially water-soluble cellulose ethers such as alkyl and hydroxyalkyl cellulose, specifically methylcellulose, hydroxypropylmethylcellulose, hydroxybutylmethylcellulose, hydroxyethylmethylcellulose, and ethylhydroxyethylcellulose, and carboxymethyl. cellulose.

Methods for preparing modified polysaccharides are well known to those skilled in the art and are discussed in the literature. See, for example, R. L. Whistler, Methods in Carbohydrate Chemistry, Vol. IV, 1964, pp. 279-331; R. L. Whistler et al., Starch-Chemistry and Technology, Vol. II, 1967, pp. 293-430; R. L. Davidson and N. Sittig, Water-Soluble Resins, 2nd Ed., 1968, Chapter 2; and R. L. Davidson, Handbook of Water-Soluble Gums and Resins, 1980, Chapters 3, 4, 12, and 13 directed to cellulose derivatives, Chapter 6 and 14 directed to gums, and Chapter 22 directed to starch.

When starch is employed as the polysaccharide, the starch may be cooked prior to derivatization, or subsequent to derivatization. Cooking at a pH of less than 7.0 simultaneously hydrolyzes the starch siloxanes to their starch silanols, creates crosslinking between starch silanols, and solubilizes and disperses the starch silanols. Any conventional cooking procedure may be used, such as jet cooking, or cooking a slurry containing the water-soluble or water-swellable starch derivatives in a boiling water bath for 20 minutes and blowing in steam to heat the slurry to about 93° C. (200° F.)

Granular starch reactions are typically accomplished in water at 20°-5020 C., preferably about 35°-45° C. Non-granular (cooked) starch reactions may be carried out at higher temperatures (e.g., up to 100° C.) so long as excessive starch degradation is avoided. The reaction mixture is preferably agitated. Reaction time may vary from about 0.5-70 hours, preferably 30-60 hours. It will depend on such factors as the amount of reagent employed, pH, temperature, scale of the reaction, and degree of substitution desired. The pH is maintained at about 10-13, preferably 11-12, during the reagent addition and during the entire reaction using an organic or inorganic base, preferably sodium, potassium, or calcium hydroxide. Sodium sulfate is typically added to the reaction to reduce swelling of the granular starch; it is not used when calcium hydroxide is the base. After completion of the reaction, the excess alkali is neutralized and the pH adjusted to about 4.8, preferably 7-8, using any conventional acid, preferably hydrochloric or sulfuric acid, prior to recovery of the starch.

The gum reactions with the organosiloxane reagents are carried out in a two-phase reaction system comprising an aqueous solution of a water-miscible solvent and a water-soluble reagent in contact with the solid gum. The water content may vary from 10 to 60% by weight depending upon the water-miscible solvent selected. If too much water is present in the reaction. system, the gum may swell and enter into solution thereby complicating the recovery and purification of the derivative. The water miscible solvent is added in the amount sufficient for the preparation of a slurry which can be agitated and pumped. The weight ratio of water-miscible solvent to gum may vary from 1:1 to 10:1, preferabiy from 1.5:1 to 5:1. Suitable water-miscible solvents include alkanols, glycols, cyclic and acyolio alkyl ethers, alkanones, dialkylformamide and mixtures thereof. Typical solvents include methanol, ethanol, isopropanol, secondary pentanol, ethylene glycol, acetone, methylethylketone, diethylketone, tetrahydrofuran, dioxane, and dimethylformamide. The reaction time may vary from 0.5-40 hours, preferably 3-6 hours, and the temperature may vary from 25°-100° C., preferably 40°-75° C.

The cellulose reactions with organosiloxane reagents are conveniently carried out using the procedure of U.S. Pat. No. 4,129,772 (issued Dec. 12, 1978 to C. P. Iovine et al.). The cellulose or cellulose derivative is suspended in water and the derivatizing reagent is added thereto. Derivatization is ordinarily carried out with agitation at temperatures of 30° C. to 85° C., adding alkali to effect the reaction. At least one of the two initial phases (i.e., the suspended cellulose or cellulose derivative or the aqueous reagent solution) contains a suitable surfactant. It is important that the organic solvent used in the initial cellulose phase be immiscible with the aqueous derivatizing reagent phase, that it have a boiling point at or above the temperature of the derivatizing reaction, and that it be insensitive to alkali. Additionally, the solvent should not dissolve the cellulose derivative as it is formed, and should not participate in the derivatization reaction.

The two phase procedure may be used to prepare starch or gum derivatives as well as cellulose derivatives. It also may be used to prepare derivatives containing substituents derived from different reagents without isolating the substitution product from each reagent. This multiple substitution may be accomplished by the sequential or simultaneous addition of several different reagents to the substrate-surfactant-alkali mixture.

After completion of the reaction the solid polysaccharide organosiloxanes may be separated, if desired, from the reaction mixture by centrifugation or filtration. Preferably, the derivative is purified by washing in a solvent in which the reagent is soluble and the polysaccharide is not. In the case of starch derivatives, water and/or a solvent are used. In the case of the gum derivatives, a solvent is used. In the case of cellulose derivatives, an aqueous solution of water miscible solvent is used. Further washing with a more anhydrous form of the same solvent may be desired for the gum derivatives. The derivatives are then air-dried using conventional equipment, such as a vacuum, drum, flash, belt or spray. drier, or by any method of drying known in the art. If the polysaccharide is in solution when derivatized, other methods of purification (e.g., dialysis) and/or recovery (e.g., precipitation) may be used.

A dry reaction process, as exemplified by U.S. Pat. No. 4,281,109 to W. Jarowenko, et al., may be used to prepare the organosiloxane derivatives herein. The reaction is typically carried out in the presence of less than 30% water and is completed in up to 2 hours at a temperature which does not exceed 200° C. The reagents typically used herein are labile at higher temperatures.

The organosiloxane-containing polysaccharide derivatives of this invention are novel compositions all having the basic structure;

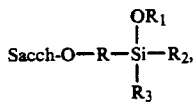

wherein Sacch- is a polysaccharide molecule; R is an organic group which is bonded to the polysaccharide by an ether or ester linkage and to the silicon by a carbon-silicon linkage; $R_1$ is a $C_{1-6}$ alkyl or alkenyl group, or an aryl, aralkyl or alkaryl group; and $R_2$ and $R_2$ are, independently, $C_1$-$C_6$ alkyl or alkenyl groups, or aryl, aralkyl or alkaryl groups, or alkoxides of $C_1$-$C_6$ alkyl or alkenyl groups, or aryl, aralkyl or alkaryl groups, or alkoxides wherein $R_2$ and $R_3$ together form a cyclic structure of at least five members. The alkyl and alkenyl chains may be straight or branched.

Typically, R is the residue of a linear or branched $C_3$-$C_{12}$ alcohol, ether, epoxide or amide. Additionally, R may be the residue of a polymer of such compounds (e.g., polyethylene glycol) wherein R may contain in excess of 12 carbon atoms, in addition to other substituents.

In a preferred embodiment of structure I, R is:

—CH₂—CH—CH₂—O—(CH₂)₃—,
      |
      OH

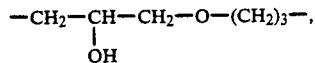

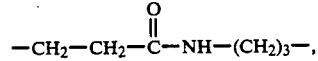

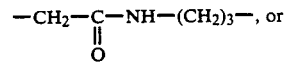

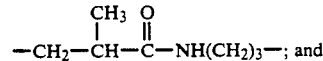

$R_1$ is —CH₃ and $R_2$ and $R_3$ are —OCH₃; or
$R_1$ is —CH₂CH₃, and $R_2$ and $R_3$ are —OCH₂CH₃; or
$R_1$ is (CH₂)₂CH₃ and $R_2$ and $R_3$ are —O—(CH₂)2CH₃; or
$R_1$ is —CH(CH₃)₂ and $R_2$ and $R_3$ are —O—CH(CH₃)₂.

This preferred embodiment may be prepared by reacting an aqueous dispersion of a polysaccharide with a reagent selected from the group consisting of 3-glycidoxypropyltrimethoxysilane (GPTMS), 3-methacrylamidopropyltriethoxysilane (MAPS), acrylamidopropyltriethoxysilane (APS) and 2-chloroacetamidopropyltriethoxysilane (GAPTES).

Other difunctional organosiloxane-containing reagents are useful herein, provided that they contain any group which will react with a hydroxyl group on the polysaccharide to form an ether or ester linkage, such that the siloxane group is attached to the polysaccharide through a carbon-silicon linkage and the siloxane is available for hydrolysis to the corresponding silanol and further reaction in glass sizing or other applications.

Such reagents must contain a polysaccharide reactive group and at least one siloxane group. The difunctional reagents useful herein are preferably soluble in water at least to the extent of 5%, by weight, at 25° C.

Suitable reagents which contain polysaccharide reactive groups include, but are not limited to, any of the well known mono- or difunctional etherifying or esterifying reagents commonly used to produce nonionic, cationic or anionic sites on the polysaccharide. Suitable polysaccharide reactive reagents include, but are not limited to, epoxide etherifying agents, epihalohydrins, halohydrins and other halogen substituted reagents, activated unsaturated compounds capable of reacting with the hydroxyl groups of the polysaccharide, organic anhydrides, beta. and gamma-halo amines, azetidines, benzyl halides, and alpha-halo esters, carbonyls, alkenes, acids and amides, alone or in combination with each other.

The other portion of the difunctional reagent comprises at least one siloxane group. Suitable substituted siloxane groups include, but are not limited to, trialkoxy, aryldialkoxy, alkyldialkoxy, diarylalkoxy, dialkylalkoxy, arylalkyalkoxy and other organosiloxane groups, alone or in combination with each other.

Preferred reagents are those containing an R group of $C_2-C_6$ and $R_1$, $R_2$ and $R_3$ groups of $C_{1-6}$, due to the relatively limited hydrophobic character of short hydrocarbon chains (visa-vis long chains) which makes these reagents more suitable for reaction with polysaccharides and for use in aqueous glass size compositions. More limited hydrophobic character may be obtained by selecting reagents substituted with hydrophilic groups (e.g., amine-, phosphate- or sulfate-containing reagents).

It will be understood by the practitioner that any combination of polysaccharide reactive group and siloxane group(s) is suitable for use herein, provided that the difunctional reagent produced by this combination is sufficiently water dispersible or soluble to permit reaction with the polysaccharide and, following preparation of the polysaccharide derivative, to permit hydrolysis of the siloxane groups to their corresponding silanol groups.

The hydrolysis of the siloxane to the silanol is accomplished by heating the organosiloxane-containing polysaccharide in the presence of water, thereby rendering the silanol polysaccharide derivative available for further reaction. It is believed that the silanol moiety bonds the polysaccharide to glass, crosslinks polysaccharide molecules, causing a rapid and significant increase in viscosity of the aqueous polysaccharide dispersion, and otherwise reacts to provide a variety of functional characteristics.

The polysaccharide graft polymers of this invention are also novel compositions, having the basic structure:

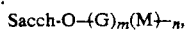  (II)

wherein Sacch- is a polysaccharide; m is zero or one; G is the residue of a polymerizable, unsaturated monomer (e.g., allyl glycidyl ether) which is bonded to the polysaccharide by an ether or ester linkage; n is greater than one; and M is the residue of one or more polymerizable, unsaturated, monomer(s), at least one of which is a siloxane-containing monomer, which have been grafted to the polysaccharide by free radical polymerization. In a preferred embodiment the siloxane-containing monomer, M, has the structure:

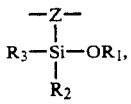

wherein Z is the residue of a polymerizable, unsaturated organic group which is bonded to the silicon by a carbon-silicon linkage; $R_1$ is a $C_1-C_6$ alkyl or alkenyl group, or an aryl, aralkyl or alkaryl group; and $R_2$ and $R_3$ are, independently, $C_{1-6}$ alkyl or alkenyl groups, or aryl, aralkyl or alkaryl groups, or alkoxides of $C_{1-6}$ alkyl or alkenyl groups, or aryl, aralkyl or alkaryl groups, or alkoxides wherein $R_2$ and $R_3$ together form a cyclic structure of at least five members. The alkyl and alkenyl chains may be straight or branched.

While siloxane-containing monomers are an essential element of the graft polymers herein, other ethylenically unsaturated monomers(M) may also be copolymerized with the siloxane-containing monomers to form the polysaccharide graft polymers herein. Such monomers include, but are not limited to, alkyl ethers; alkyl acrylates; carboxyalkyl ethers; vinyl esters of carboxylic acids; carboxylic acids; dicarboxylic acids and their esters; olefins; and esters, amides and salts thereof.

In one preferred embodiment of Structure II, Z is:

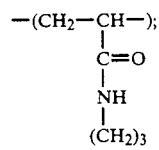

and $R_1$ is $CH_3$ and $R_2$ and $R_3$ are $-OCH_3$; or $R_1$ is $CH_2CH_3$, and $R_2$ and $R_3$ are $OCH_2CH_3$, or $R_1$ is $(CH_2)_2CH_3$ and $R_2$ and $R_3$ are $-O-(CH_2)_2CH_3$ or $R_1$ is $-CH-(CH_3)_2$ and $R_2$ and $R_3$ are $-O-CH-(CH_3)_2$. In the manner illustrated below, this preferred graft polymer is prepared by, first, reacting the polysaccharide with an ethylenically or allylically unsaturated monomer, such as allyl glycidyl ether (—G—), and, second, grafting onto the polysaccharide derivative one or more polymerizable monomer(s), at least one of which is a siloxane-containing monomer (—M—) selected from the group of reagents described above for preparation of polysaccharide derivatives.

The two step graft copolymerization occurs in the following manner:

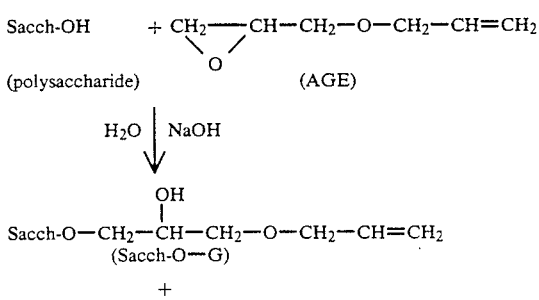

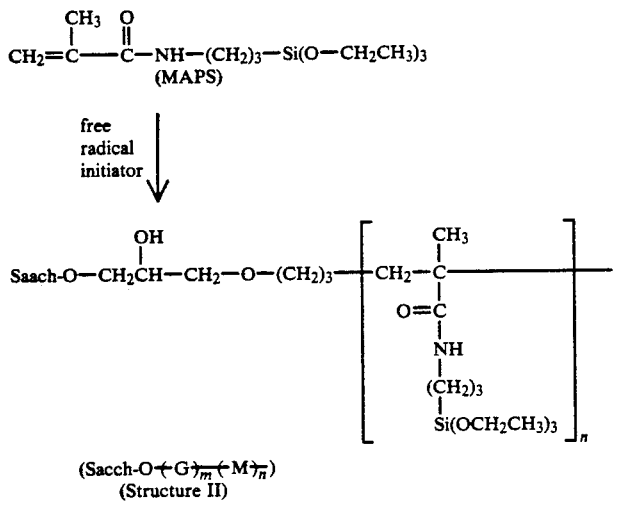

(Sacch-O⁺G⁾ₘ⁺M⁾ₙ)
(Structure II)

The practitioner will recognize that the graft polymer of Structure II also may be prepared without first reacting the polysaccharide with an ethylenically or allylically unsaturated monomer (G). In such a case, m is zero and a suitable, polymerizable, unsaturated, siloxane-containing monomer is permitted to polymerize in the presence of the polysaccharide and, optionally, in the presence of other monomers. Thus, a polymer is grafted directly onto the polysaccharide during polymerization employing conventional methods. Siloxane-containing monomers suitable for use under such conditions include, but are not limited to, methacrylamidopropyl triethoxysilane, acrylamidopropyl triethoxysilane, diallylaminopropyl trimethoxysilane, 3-(trimethoxy)silylpropyl methacrylate, and 3-(trimethoxy)-silylpropyl acrylate.

When preparing the polysaccharide graft polymer by the two step process illustrated above, the polysaccharide derivative may be used in any form so long as that form renders the polymer molecules available for graft polymerization. For example, in a preferred embodiment an acid-converted starch derivative (85 WF waxy maize starch allyl glycidyl ether derivative) is gelatinized by cooking in water to yield an aqueous starch dispersion. Water Fluidity (or WF) is a numerical index used to describe the amount of starch conversion, and it is inversely related to the starch viscosity. In such a dispersion, the gelatinized starch molecules are more readily accessible for graft copolymerization than are the starch molecules of an aqueous granular starch slurry.

The amount of polysaccharide may vary from 5 to 95%, preferably from 20 to 50%, by weight, of the final graft polymer.

Suitable monomers for preparing the siloxane-containing polysaccharides herein include any water-soluble, siloxane-containing, unsaturated compounds that are capable of free radical polymerization. Water soluble is defined herein to mean monomers which have a minimum solubility of 5% by weight in water at 25° C. Such monomers contain linkages which include, but are not limited to, acrylamido, methacrylamido, diallylamino, and acryloyl and methacryloyl ester linkages (e.g., acrylamido-propyltriethoxy silane). Various other water-soluble monomers suitable for graft polymerization with polysaccharides are known to those skilled in the art and may be employed herein. If the graft polymer is prepared in a solvent or a water miscible solvent system, water-insoluble monomers may be employed.

The monomers listed herein may be used in any form desired for a particular application. Thus, where a monomer is listed herein in its acid form, the salt form is meant to be included, and vice versa.

Method for preparing graft polymers of polysaccharides such as starches, cellulose, and gums are well known in the literature. See, for example, *Block and Graft Copolymerization*, Vol. 1, R. J. Ceresa, ed., John Wiley and Sons (1973). Modification of starch by graft polymerization is described at pages 22-47 to 22.54 in Chapter 22: Starch and its Modifications in *Handbook of Water-Soluble Gums and Resins*, edited by Robert L. Davidson, McGraw-Hill Book Co., New York 1980. Methods for preparing graft polymers include polymerization in water, in water-solvent mixtures, and in the dry state and may be initiated by mechanical, chemical, and irradiative techniques.

The preferred method of preparing the siloxane-containing polysaccharide graft polymers is free radical polymerization. Free radical initiating methods include physical (e.g., irradiation) and chemical methods (e.g., the use of catalysts). Suitable catalysts include those of the type that establish mild oxidizing conditions at the concentrations used in the reaction mixture and are usually classified as free radical formers or sometimes called peroxidic catalysts. This class of catalysts include, among others, hydrogen peroxides, aqueous soluble organic peroxides, hydroperxides, persulfate salts such as potassium and ammonium persulfate, ceric ions, and redox catalysts. Other free radical catalysts are those classified as water soluble "azo" catalysts, such as 2,2'-azobis(isobutyronitrile). The reaction is typically carried out until all of the monomer is consumed. Typically, the starch grafts are prepared by suspending the starch derivative in an aqueous solution, heating the suspension until the starch is gelatinized, adding the monomer, and then adding the free radical catalyst. Granular starch derivatives can also be used. They may be first heated in water at 50° C. for one hour to swell before cooling to room temperature for the subsequent polymerization reaction.

In addition to preparing the above organosiloxane derivatives and graft polymers, modified siloxane-containing polysaccharides may be prepared which also contain other substituent groups, such as hydroxyalkyl groups (e.g., hydroxypropyl ether groups), carboxyalkyl ether groups (e.g., carboxymethyl), ester groups (e.g., acetate groups), and amino groups (e.g., diethylaminoethyl ether groups, or 3-trimethylammonium chloride)-2-hydroxypropyl ether groups), introduced prior to or subsequent to reaction with the organosiloxane reagent, or introduced simultaneously by reaction with the organosiloxane reagent and other derivatizing reagent. In a preferred embodiment the derivative is prepared before or simultaneously with the starch organosiloxane reaction. The practitioner will recognize that reactions with reagents introducing labile ester groups should be carried out after the other derivatizations to avoid ester hydrolysis under the alkaline conditions used to prepare other derivatives.

In addition to being useful in glass sizing compositions, the organosiloxane-containing polysaccharide derivatives and graft polymers are also useful in applications where conventional water-soluble or water. swellable polysaccharide derivatives are useful. For example, they are useful as coatings, adhesives, and paper and textile additives. When used as a paper additive, the derivatives typically contain cationic or cationogenic groups in addition to the siloxane groups. These include diethylaminoethyl ether groups introduced by reaction of the polysaccharide with 2-diethylaminoethyl chloride hydrochloride (DEC) or 3-(trimethylammonium chloride)-2-hydroxypropyl ether groups introduced by reaction with 3-chloro-2-hydroxypropyl trimethylammonium chloride.

The siloxane polysaccharide compositions described herein may be used in paper-making as beater additives, or as additives to the pulp at any point in the paper-making process prior to the ultimate conversion of the wet pulp into a dry web or sheet. Thus, for example, they may be added to the pulp while the latter is in the hydropulper, beater, various stock chests, or headbox. The compositions may also be sprayed onto the wet web.

The siloxanes herein may be effectively used for addition to pulp prepared from any type of cellulosic fibers, synthetic fibers, or combinations thereof. Among the cellulosic materials which may be used are bleached and unbleached sulfate (kraft), bleached and unbleached sulfite, bleached and unbleached soda, neutral sulfite, semi-chemical chemiground wood, ground wood or any combination of these fibers. Fibers of the viscose rayon or regenerated cellulose type may also be used if desired.

Any desired inert mineral fillers may be added to the pulp which is to be modified with the siloxanes herein. Such materials include clay, titanium dioxide, talc, calcium carbonate, calcium sulfate and diatomacous earths. Rosin or synthetic internal size may also be present if desired.

The proportion of the siloxane-containing polysaccharide to be incorporated into the paper pulp may vary in accordance with the particular pulp involved and the properties desired (e.g., wet strength, temporary wet strength, or dry strength). In general, it is preferred to use about 0.1.–10% preferably about 0.25–5% of the composition, based on the dry weight of the pulp. Within this preferred range the precise amount which is used will depend upon the type of pulp being used, the specific operating conditions, the particular end use for which the paper is intended, and the particular property to be imparted. The use of amounts greater than 5%, based on the dry weight of the pulp is not precluded, but is ordinarily unnecessary in order to achieve the desired results.

It can be appreciated by the practitioner that a large number of variations may be effected in selecting the siloxane derivatizing reagents, reacting them with the polysaccharides, and utilizing the siloxane compositions as wet end additives for paper in accordance with the procedure described above without materially departing from the scope and spirit of the invention. Such variations will be evident to those skilled in the art and are to be included within the scope of the invention.

The aqueous glass fiber forming size composition ("size composition") of the present invention will typically have a solids content of about 1–10%, by weight, wherein the siloxane-containing starch derivative or graft polymer is present in an amount ranging from about 40–70%, and preferably 60% of the total composition. Potato and high amylose (i.e., more than 40% amylose) starches are preferred.

Preferably, the size composition contains on the order of about 6% solids. The total solids should be at a level whereby the viscosity of the size dispersion is acceptable for application to the glass filaments (i.e., not exceeding 25 centipose at 60° C.).

The nonionic oils used for the size composition may be selected from vegetable, animal, or mineral oils, and are preferably hydrogenated to reduce their flowability. The oils are preferably fatty triglycerides including, for example, hydrogenated soybean oil, hydrogenated corn oil, glycerol tristearate, hydrogenated glycerol trioleate, and the like. The oil will typically be present in the size formulation in amounts ranging from about 25% of the total composition and is preferably employed in an amount ranging from 30 to 65%, based on the total starch concentration.

The size composition also preferably contains an emulsifying agent, typically present in amounts ranging from about 2–8% of the total size composition. HLB values between about 8 and 17 are most suitable with polyoxyalkylenesorbitans being preferred. Such emulsifiers are commercially available and include TWEEN 81 ® from ICI Americas Inc., which is a polyethylene derivative of sorbitan mono-oleate. TRITON ® emulsifiers, polyoxyethylene derivatives of alkyl substituted phenols, obtained from Rohm and Haas are also useful herein.

Cationic glass fiber lubricants used in the art to serve primarily as a lubricant prior to the time the size fibers are dried may optionally be employed in the present composition in an amount of less than about 15% of the total size composition. Such lubricants include, for example, alkyl imidazoline derivatives (i.e., the reaction product of tetra ethylene pentamine and stearic acid) and quaternary pyridinium compounds.

Other conventional size composition additives including, for example, solid unctuous material such as wax, fat, or gelled oils which do not flow at application temperatures; secondary film formers such as gelatin, polyvinyl alcohol and polyacrylates; silane coupling agents; mildew preventatives; and fungicides may also be employed in the present size composition in conventional amounts.

The size compositions herein may be prepared and applied to the glass fibers upon formation by conventional means. An aqueous slurry of the starch derivative is preferably cooked for a period of time to gelatinize a portion of the starch while maintaining a quantity of the starch in a swollen, unburst granular form. Thereafter, an emulsion of the nonionic oil and emulsifiers are typically added to the starch slurry along with any additional size ingredients prior to application. The size composition may then be applied at an elevated temperature (typically 55°-60° C.) by a suitable application method, such as by the employment of an apron type applicator or other conventional means including a padder or roll apparatus, an immersion apparatus or by spray or jet means, all of which are well known to those skilled in the art.

In the examples which follow, all parts and percentages are given by weight and all temperatures are in degrees Celsius unless otherwise noted. Reagent percentages are based on dry polysaccharide.

The nitrogen content of the reagents and resulting siloxanes was measured by the Kjeldahl method and is based on dry polysaccharide.

The presence of organosiloxane groups was determined qualitatively by observing the viscosity increase caused by cooking an aqueous slurry of the polysaccharide derivative or graft polymer to effect hydrolysis of the siloxanes to their silanols and crosslinking between the silanols. The Brookfield viscosity test was carried out by slurrying 40 g of the polysaccharide siloxane in sufficient distilled water to give 100 g. The pH was adjusted to 5.0 or 7.0 with hydrochloric acid or to 11.0 with sodium hydroxide. The polysaccharide was dispersed and crosslinked by cooking in a boiling water bath for 20 minutes. The solids were determined and adjusted and the viscosity was measured using a #7 spindle at 20 rpms and 25° C.

EXAMPLE I

This example describes the preparation of a siloxane-containing derivative having the structure:

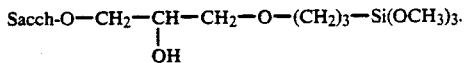

Sodium hydroxide (0.8 g) (0.8% solution based on starch) was dissolved in 150 ml of distilled water in a sealed pint jar equipped with a magnetic stir bar and stirred until dissolved. A total of 100 g of acid-converted (85 WF) waxy maize starch was added quickly and the slurry was shaken to a uniform consistency. The appropriate amount (1.0 to 4.0 g) of 3-glycidoxypropyl-trimethoxysilane (GPTMS) was added to the container and the container was sealed. The reaction mixture was heated to 40° C. and held at 40° C. in a tumbler for 60 hours. The mixture was then cooled to room temperature and the pH adjusted to 7.5 with dilute hydrochloric acid. The starch was then filtered and washed three times with 150 ml of water and twice with 150 ml of isopropyl alcohol and air dried.

Aqueous slurries of the starches (45% solids) were cooked in a boiling water bath for 20 minutes and analyzed for viscosity changes. Results are summarized in Table I. The maximum viscosity measurable with the Brookfield instrument is 200,000 centipoise. The results show that at each pH measured, the viscosity increases with increasing organosiloxane treatment levels. It is believed that the observed viscosity increase is due to increases in silanol-silanol crosslinking upon cooking as the degree of siloxane substitution on the starch increases. Thus, these results show that the degree of substitution increased with increasing organosiloxane treatment levels.

TABLE I

| Starch-GPTMS Derivatives | | |
|---|---|---|
| GPTMS Treatment Level % | pH | Viscosity cps |
| Control | 5.0 | 4,000 |
| " | 7.0 | 3,000 |
| " | 11.0 | 3,000 |
| 1 | 5.0 | 9,000 |
| " | 7.0 | 12,000 |
| " | 11.0 | 10,000 |
| 2 | 5.0 | 200,000* |
| " | 7.0 | 102,000 |
| " | 11.0 | 7,000 |
| 4 | 5.0 | 200,000* |
| " | 7.0 | 200,000* |
| " | 11.0 | 200,000* |

*Maximum Brookfield viscosity reading.

EXAMPLE II

This example describes the preparation of a siloxane-containing starch derivative having the structure:

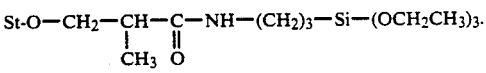

Part A—Preparation of 3-methacrylamidopropyltriethoxysilane (MAPS).

A solution of 3-aminopropyltriethoxysilane (20.0 g) in toluene (200 ml) was added to a 500 ml three neck flask equipped with magnetic stir bar, addition funnel, and nitrogen inlet. A total of 9.11 g of triethylamine was added to the solution and the solution was cooled to 0° C. in an ice bath. A total of 9.41 g of methacryloyl chloride was added dropwise to the reaction by the addition funnel at a rate such that the temperature did not exceed 5° C. The reaction was stirred overnight with gradual warming to room temperature. The reaction mixture was then washed 4 times with 200 ml of ice water, dried over magnesium sulfate and concentrated under vacuum. The yield was 38.4 percent and the reaction product was used without further purification.

Part B—Preparation of a Siloxane-Containing Starch Ether Derivative.

A pint jar equipped with a magnetic stir bar was used as a reaction container. A total of 0.8 g of sodium hydroxide was added to 150 ml of water in the jar and stirred until dissolved. Waxy maize starch (100 g) was added quickly and the slurry shaken to a uniform consistency. The reagent (10 g), from part A above, was added to the slurry and the jar was sealed and placed in a tumbler at 40° C. for 48 hours. The starch was then cooled to room temperature, filtered, washed 3 times with water (150 ml), two times with isopropanol (150 ml) and air dried. The reaction product was analyzed for nitrogen content. The waxy maize-MAPS reaction product contained 0.092% nitrogen. An acid-converted (85 WF) waxy maize-MAPS reaction product which was prepared in an identical manner contained 0.30% nitrogen. In contrast, an acid-converted (85 WF) waxy maize control contained only 0.02% nitrogen. Thus, the MAPS derivative was successfully prepared from waxy maize starch, and, at a higher degree of substitution, from acid-converted waxy maize starch.

Part C—Preparation of 3-chloroacetamidopropyl-triethoxysilane (CAPTES) and Its Starch Derivative Reaction of 2-chloroacetyl chloride and 3-aminopropyltriethoxy silane was accomplished using a procedure similar to that described in part A of this example. The starch reaction required the use of 3 percent sodium hydroxide and 30 percent sodium sulfate to limit starch granule swelling, but all other parameters were identical to those set forth in part B above. The starch reaction product contained 0.07 percent nitrogen.

EXAMPLE III

This example demonstrates that the siloxane group is not bonding directly with the polysaccharide under reaction conditions utilized herein. An organosiloxane reagent which did not contain a polysaccharide reactive group capable of forming an ether or ester bond with the polysaccharide (i.e., 3-aminopropyltriethoxysilane (APTES)) was permitted to react with acid-converted (85 WF) waxy maize starch.

The reaction was carried out as detailed in Example II, Part B. The starch which was permitted to react with APTES had the same nitrogen content as the starch control, thereby demonstrating that the siloxane functional group of the APTES reagent had not reacted with the starch. Thus, no direct bonding of the siloxane with the hydroxyls of the starch molecule had occurred under these reaction conditions and, therefore, the increased nitrogen content observed in starches reacted with suitable polysaccharide reactive groups (i.e., MAPS and CAPTES) could not have been due to direct bonding of the siloxane with a starch hydroxyl group.

EXAMPLE IV

This example illustrates the preparation of a siloxane-containing ester derivative having the structure:

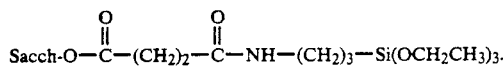

Part A—Preparation of 3-Carboacetoxy-N-Propyl-triethoxysilyl Propanamide.

A total of 22.1 g (0.1 M) of aminopropyltriethoxysilane is added to a 500 ml round bottom flask, equipped with a magnetic stir bar, addition funnel, nitrogen inlet and cooling bath, along with 100 ml of toluene and 25 g (0.24 M) of triethylamine. The solution is cooled to less than 5° C. and succinic anhydride is added dropwise such that the temperature does not exceed 10° C. The reaction is allowed to warm slowly to room temperature, and after the reaction goes to completion, it is cooled to 5° C. and 7.8 g (0.1 M) acetyl chloride is added dropwise keeping the temperature below 10° C. The reaction is warmed to room temperature and stirred for two hours. The product is washed with ice water (3×75 ml), dried over magnesium sulfate and the solvent is removed under vacuum.

Part B—Preparation of a Siloxane Starch Derivative.

A total of 150 ml of distilled water is added to a beaker equipped with an overhead stirrer and pH meter. A total of 100 g of corn starch is slurried with the water and the pH is adjusted to 7.5 using 3% sodium hydroxide. A total of 9 g of the siloxane reagent (prepared in Part A of this Example) is added in three equal portions of 3 g each at half hour intervals. The pH is maintained at 7.5 using sodium hydroxide until no change in pH is detected after one hour. The starch is filtered, washed with water (100 ml), reslurried in water and the pH is adjusted to 6.5 with dilute hydrochloric acid. The starch is filtered, washed with water (3×100 ml) and air-dried to less than 15% moisture.

EXAMPLE V

This example illustrates the preparation of a siloxane-containing derivative of dispersed (cooked, nongranular) starch.

A 100 g portion of acid-converted starch (85 WF waxy maize) was slurried in 150 ml of water and cooked for 20 minutes in a boiling water bath. The cooked starch dispersion was then cooled to room temperature. A total of 0.8 g of sodium hydroxide and 10 g of methacrylamidopropyl triethoxysilane was added and mixed in a pint jar. The jar was sealed, placed in a tumbler and heated to 45° C. for 18 hours. The reaction was then cooled to room temperature and neutralized to pH 7.0 with hydrochloric acid. The starch derivative was recovered by acetone precipitation and air-dried. Nitrogen content of the starch derivative was 0.377 percent on a dry weight basis, indicating that the MAPS derivative had been prepared from dispersed starch.

EXAMPLE VI

This example describes the graft polymerization of organosiloxanes with a starch derivative.

Acid-converted waxy maize starch (85 WF) was derivatized with allyl glycidyl ether using the procedure described in Example I. A total of 50 g of this starch derivative was cooked in 250 mls of water in a boiling water bath for twenty minutes and then introduced into a 1000 ml Morton flask equipped with a reflux condenser, addition funnel, thermometer, and overhead stirrer. An appropriate amount of MAPS reagent (5.0 g), prepared as in Example II, Part A, above, was added to the reaction flask and the pH was adjusted to 7.0. Ammonium persulfate (0.4 g) was dissolved in 24 ml of degassed water and added to the reaction in one-third increments over three hours. The reaction was stirred for an additional four hours, inhibited with hydroquinone monoethyl ether, and then the graft polymer was precipitated from acetone. The graft polymer was air dried and analyzed for nitrogen. The reaction product contained 0.55% nitrogen, indicating that a starch graft polymer had been prepared.

EXAMPLE VII

This example describes preparation of a siloxane-containing cellulose derivative having the structure:

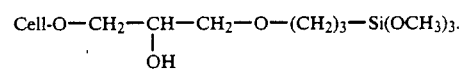

A total of 1000 ml of distilled water and 0.8 g of sodium hydroxide were added to a half-gallon glass jar and stirred until the sodium hydroxide was dissolved. Alpha cellulose (100 g) was added to the reaction jar and the jar was shaken until the slurry was of a uniform consistency. The silane reagent (GPTMS) (5 g) was added to the slurry and the jar was sealed and mixed in a tumbler at 40° C. for 18 hours. The reaction jar was then cooled to room temperature, neutralized to pH 7.0 with 10% hydrochloric acid, filtered and washed three times with water (500 ml), two times with isopropanol (500 ml) and air-dried. In a 10% solids aqueous dispersion at pH 5.0, a cellulose control sample did not disperse. In contrast, under the same conditions, the reaction product dispersed to yield a thin texture, indicating that the cellulose-GPTMS derivative had been prepared.

EXAMPLE VIII

This example describes the preparation of a siloxane-containing guar gum derivative having the structure:

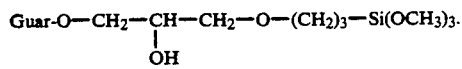

Guar-O—$CH_2$—CH—$CH_2$—O—$(CH_2)_3$—$Si(OCH_3)_3$.
 |
 OH

An acetone/water mixture was prepared by adding 140 ml of acetone to 60 ml of distilled water and the mixture was added to a single neck round-bottom flask equipped with an overhead stirrer and a reflux condenser. Sodium hydroxide (1.0 g) was added and the mixture was stirred until it dissolved. A total of 100 g of guar gum was added to the reaction along with the GPTMS reagent (5g). The reaction was heated at reflux for 4 hours, cooled, filtered, washed three times with acetone/water (100 ml) and air-dried. In a 3% solids aqueous dispersion at pH 5.0, a guar gum control yielded a thin, long texture. In contrast, under the same conditions, the reaction product dispersed to yield a heavy, suave texture, indicating that the guar gum-GPTMS derivative had been prepared.

EXAMPLE IX

This example illustrates the utility of siloxane-containing starches in glass coatings.

A slurry containing 5% solids (5 parts starch/95 parts water) was prepared with a siloxane-containing starch prepared by the method of Example I. The pH was adjusted to 9.0 with dilute sodium hydroxide to prevent crosslinking of the starch during cooking. The starch slurry was then heated in a boiling water bath for 30 minutes to partially disperse the starch. Once dispersed, a starch film was cast onto a glass plate. The pH of the starch was lowered to 5.0 with dilute hydrochloric acid either before or after casting the films. An atomizer was used to apply the acid to the film. Film thicknesses were in the range of 5-30 mils (thousands of an inch). This variable had no effect on the glass adhesion.

The subjective evaluations are summarized in Table II. A rating of excellent indicated the film could not be removed without breaking the supporting glass. A rating of very good indicated the film was the most difficult to remove without damaging the glass substrate. A rating of good indicated that there was an improvement in glass adhesion over that observed with the unmodified starch. A rating of average indicated the film was as easily removed from the glass as an unmodified corn or waxy maize starch.

TABLE II

| Starch | Percent Treatment | Glass Adhesion |
|---|---|---|
| High Amylose | 0 | Average |
| High Amylose Fluidity | 0 | Average |
| High Amylose Fluidity | 1 | Average |
| High Amylose Fluidity | 2.5 | Good |
| High Amylose Fluidity | 5 | Good |
| Potato | 0 | Good |
| Potato Fluidity | 0 | Good |
| Potato Fluidity | 1 | Very Good |
| Potato Fluidity | 5 | Excellent |

EXAMPLE X

This example illustrates the preparation of a typical glass fiber forming size composition using the siloxane-containing starches disclosed herein.

| Size Composition | |
|---|---|
| Ingredient | Percent, by weight |
| Siloxane-containing Starch | 4.9 |
| Hydrogenated vegetable oil | 1.18 |
| Polyoxyethylene sorbitan monooleate | 0.19 |
| Tetraethylene pentamine distearate | 0.22 |
| Polyethylene glycol | 1.15 |
| Water | Remainder |

A size composition is prepared from the above ingredients by placing all of the starch and one-half of the water in a suitable receptacle, adjusting the pH to 9.0±2.0 with calcium hydroxide or other base, and cooking the starch. After cooking, the pH is lowered to 5.0±2.0 with hydrochloric acid. The vegetable oil and polyoxyethylene sorbitan monooleate are then separately admixed at 150°-170° F., agitated until the inversion of the emulsion and preferably homogenized at 2000 pounds per square inch. The emulsion, the tetraethylene pentamine distearate and the remainder of the water are added to the starch cook and agitated. While the starch in the above-described process is cooked in conventional equipment using conventional techniques as, for example, an open tank or receptacle at substantially atmospheric temperature and pressure, other suitable methods of cooking the starch may be used.

EXAMPLE XI

This example illustrates the paper making applications of cationic starches modified with siloxanes by the method of Example I.

Cationic, siloxane-containing starch derivatives were prepared by the method of Example I. Samples of these derivatives were prepared for testing in accordance with the TAPPI T494 method ("Tensile Breaking Properties of Paper and Paperboard [Using Constant rate of Elongation Apparatus], TAPPI T494, 1982). A total of 1.0 g of a cationic starch siloxane derivative was dissolved in 99.0 g of water and the pH was adjusted to 7.0 using hydrogen chloride or sodium hydroxide. The mixture was cooked in a boiling water bath for a total of 30 minutes with stirring for the first three minutes. The starch was then cooled and added to the pulp in a head box (at the rate of 0.5 percent starch based on dry weight of paper). Tensile strength of the final sheet was measured using a Model II Intellect Machine (Thwing-Albert Instrument Company, Philadelphia, Pa.), and results are summarized in Table III. These results indicate that dry strength can be improved by having siloxane present on cationic starch.

TABLE III

| | % Siloxane Treatment | Paper Dry Strength grams |
|---|---|---|
| Cationic waxy maize | 0.0 | 1586 |
| Cationic waxy maize (50 WF) | 1.0 | 1765 |
| Cationic waxy maize (50 WF) | 5.0 | 1825 |

Now that the preferred embodiments of the invention have been described in detail, various modifications and improvements thereon will become readily apparent to those skilled in the art. Accordingly, the spirit and scope of the present invention are to be limited only by the appended claims and not by the foregoing specification.

I claim:

1. A polysaccharide graft polymer, comprising the structure:

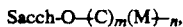

wherein Sacch- is a polysaccharide; m is zero or one; G is the residue of a polymerizable, unsaturated monomer which is bonded to the polysaccharide by an ether or ester linkage; n is greater than one; and M is the residue of one or more polymerizable, unsaturated, monomer(s), at least one of which is a siloxane-containing monomer, which have been grafted to the polysaccharide by free radical polymerization.

2. The polymer of claim 1, wherein G is derived from allyl glycidyl ether; and M comprises the structure:

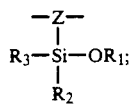

wherein Z is the residue of a polymerizable, unsaturated organic group which is bonded to the silicon by a carbon-silicon linkage; $R_1$ is a straight or branched $C_{1-6}$ alkyl or alkenyl group, or an aryl, aralkyl or alkaryl group; and $R_2$ and $R_3$ are, independently, straight or branched $C_{1-6}$ alkyl or alkenyl groups, or aryl, aralkyl or alkaryl groups, or alkoxides of straight or branched $C_{1-6}$ alkyl or alkenyl groups, or aryl, aralkyl or alkaryl groups, or alkoxides wherein $R_2$ and $R_3$ together form a cyclic structure of at least five members.

3. The polymer of claim 2, wherein

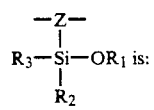

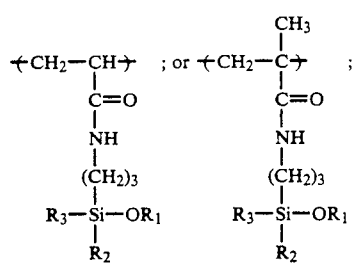

4. The polymer of claim 3, wherein $R_1$ is —$CH_3$ and $R_2$ and $R_3$ are —$OCH_3$; or wherein $R_1$ is —$CH_2$—$CH_3$, and $R_2$ and $R_3$ are —$OCH_3$; or wherein $R_1$ is —($CH_2)_2$—$CH_3$ and $R_2$ and $R_3$ are —$O(CH_2)_2$—$CH_3$; or wherein $R_1$ is —CH—$(CH_3)_2$ and $R_2$ and $R_3$ are —O—CH—$(CH_3)_2$.

5. A glass forming size composition, comprising a aqueous dispersion of a starch graft polymer having the structure:

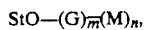

wherein StO is a starch molecule; G is the residue of a polymerizable, unsaturated monomer which is bonded to the starch by an ether or ester linkage; m is zero or one; M is the residue of one or more polymerizable, unsaturated monomer (s), at least one of which is a siloxane-containing monomer, which has been grafted to the starch by free radical polymerization; and n is greater than one.

6. The polymer of claim 5, wherein G is derived from allyl glycidyl ether; and M comprises the structure:

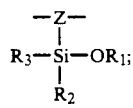

wherein Z is the residue of is a polymerizable, unsaturated organic group which is bonded to the silicon by a carbon-silicon linkage; $R_1$ is a straight or branched $C_1$-$C_6$ alkyl or alkenyl group, or an aryl, aralkyl or alkaryl group; and $R_2$ and $R_3$ are, independently, straight or branched $C_1$-$C_6$ alkyl or alkenyl groups, or aryl, aralkyl or alkaryl groups, or alkoxides of straight or branched $C_1C_6$ alkyl or alkenyl groups, or aryl, aralkyl or alkaryl groups, or alkoxides wherein $R_2$ and $R_3$ together form a cyclic structure of at least five members.

7. The size composition of claim 5 comprising 40-70% of the aqueous dispersion of the starch graft polymer; 15-40% of a nonionic oil; 2-8% of an emulsifier; and 5-15% of a cationic lubricant, with the percentages being by weight and totalling 100%.

8. The size composition of claim 5, wherein the starch is a high amylose corn, potato, or waxy maize starch.

9. A method of sizing glass fibers, comprising applying the glass forming size composition of claim 5 onto the fibers during formation.

10. The sized glass fiber produced according to the method of claim 9, characterized by improved adhesion of the size composition to the glass fiber.

11. A method for making paper, comprising the addition to the paper stock of an effective amount of an aqueous dispersion of a starch graft polymer having the structure; StO—(G)$_{\overline{m}}$(M)—$_n$, wherein StO— is a starch molecule; G is the residue of a polymerizable, unsaturated monomer which is bonded to the starch by an ether or ester linkage; m is zero or one; M is the residue of one or more polymerizable, unsaturated, monomer(s), at least one of which is a siloxane-containing monomer, which have been grafted to the starch by free radical polymerization; and n is greater than one.

12. Paper made by the method of claim 11.

* * * * *